US009962446B2

(12) United States Patent
Grasman et al.

(10) Patent No.: US 9,962,446 B2
(45) Date of Patent: May 8, 2018

(54) SOLID DISPERSION COMPRISING A HIGHLY SUBSTITUTED HYDROXYALKYL METHYLCELLULOSE

(71) Applicant: DOW GLOBAL TECHNOLOGIES LLC, Midland, MI (US)

(72) Inventors: Nicholas S. Grasman, Midland, MI (US); Steven J. Guillaudeu, Midland, MI (US); Mark J. Hall, Gaylord, MI (US); Uma Shrestha, Bay City, MI (US); Maureen L. Rose, Midland, MI (US); William W. Porter, III, Midland, MI (US); Wesley J. Spaulding, Freeland, MI (US); Kevin P. O'donnell, Midland, MI (US); True L. Rogers, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 106 days.

(21) Appl. No.: 14/413,241

(22) PCT Filed: Jul. 12, 2013

(86) PCT No.: PCT/US2013/050213
§ 371 (c)(1),
(2) Date: Jan. 7, 2015

(87) PCT Pub. No.: WO2014/014752
PCT Pub. Date: Jan. 23, 2014

(65) Prior Publication Data
US 2015/0140091 A1 May 21, 2015

Related U.S. Application Data

(60) Provisional application No. 61/672,409, filed on Jul. 17, 2012.

(51) Int. Cl.
*A61K 9/14* (2006.01)
*A61K 47/38* (2006.01)
*A61K 9/16* (2006.01)
*A61K 9/48* (2006.01)
A61K 31/343 (2006.01)
A61K 31/58 (2006.01)
A61K 31/4166 (2006.01)

(52) U.S. Cl.
CPC ............ *A61K 47/38* (2013.01); *A61K 9/146* (2013.01); *A61K 9/1652* (2013.01); *A61K 9/4891* (2013.01); *A61K 31/343* (2013.01); *A61K 31/4166* (2013.01); *A61K 31/58* (2013.01)

(58) Field of Classification Search
CPC ...... A61K 9/146; A61K 9/1652; A61K 47/38; A61K 31/38; A61K 31/343; A61K 31/4166
See application file for complete search history.

(56) References Cited

U.S. PATENT DOCUMENTS

| 4,316,982 A | 2/1982 | Holst et al. |
| 4,614,545 A | 9/1986 | Hess |
| 7,070,828 B2* | 7/2006 | Sheskey ............... A61K 9/2866 427/2.14 |
| 7,081,255 B2* | 7/2006 | Baert .................... A61K 9/146 424/464 |
| 2015/0065548 A1* | 3/2015 | Adden .................... A61K 9/08 514/391 |

FOREIGN PATENT DOCUMENTS

| EP | 0210917 A2 | 2/1987 |
| EP | 0872233 A1 | 10/1998 |
| EP | 1141029 B1 | 10/2001 |
| EP | 1423433 B1 | 6/2004 |
| WO | 9744014 A1 | 11/1997 |
| WO | 0185135 A1 | 11/2001 |
| WO | 03048147 A2 | 6/2003 |
| WO | 2005115330 A2 | 12/2005 |
| WO | 2008047201 A2 | 4/2008 |

OTHER PUBLICATIONS

Technical Handbook of METHOCEL cellulose ethers (online:downloaded on Jan. 19, 2018 from http://msdssearch.dow.com/PublishedLiteratureDOWCOM/dh_096d/0901b8038096d9ff.pdf ; Sep. 2002, 8 pages.*
Europ. J. of Pharma. and Biopharma., 54, 2002, p. 107-117, Breitenbach, Melt extrusion.
Z.Anal.Chem. 286, 1977, p. 161-190, Bartelmus et al., Die Analytik von Celluloseäthergruppen.
Int. J. of Pharma., 251, 2003, p. 165-174, Verreck et al., Characterization of solid dispersions . . . .
Int. J. of Pharma. 212, 2001, p. 213-221, Raghavan et al., Crystallization of hydrocortisone . . . .
J. of Drug Targeting, 18(10), 2010, p. 704-731, Warren et al., Using polymeric precipitation inhibitors . . . .
Mol. Pharma. 5,6, 2008, p. 1003-1019, Friesen et al., Hydrosypropyl Methylcellulose Acetate . . . .
Drug Discovery Today, 2001, Mooter, The use of amorphous solid dispersions . . . .
Pharma. Research, 26, 6, 2009, Curatolo et al., Utility of Hydroxypropylmethylcellulose . . . .
J. of Pharma. Science, 97, 8, 2008, Feng et al., Process Induced Disorder in Crystalline Materials . . . .

* cited by examiner

*Primary Examiner* — Lakshmi Channavajjala

(57) ABSTRACT

A solid dispersion comprising at least one active ingredient in at least one hydroxyalkyl methylcellulose having a DS of from 1.0 to 2.7 and an MS of from 0.40 to 1.30, wherein DS is the degree of substitution of methoxyl groups and MS is the molar substitution of hydroxyalkoxyl groups, can be produced by extrusion or spray-drying.

17 Claims, No Drawings

SOLID DISPERSION COMPRISING A HIGHLY SUBSTITUTED HYDROXYALKYL METHYLCELLULOSE

FIELD

This invention relates to solid dispersions comprising an active ingredient in a hydroxyalkyl methylcellulose and to processes for producing said dispersions.

INTRODUCTION

A large number of presently known drugs have a low solubility in water, and thus complex techniques are required to prepare a suitable dosage form. Much research is spent on the use of pharmaceutically acceptable water-soluble polymers in combination with drugs of low water solubility. The use of water-soluble polymers aims at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon administration. However, simple blending of a water-soluble polymer with a drug of low water solubility generally does not reduce the crystallinity of the drug nor generally improve said drug's solubility.

G. Van den Mooter, "The use of amorphous solid dispersions: A formulation strategy to overcome poor solubility and dissolution rate", *Drug Discov Today: Technol* (2011), doi:10.1016/j.ddtec.2011.10.002, discusses the preparation of amorphous solid dispersions to increase the bioavailability of poorly soluble drugs by improving their rate and extent of dissolution. The two most applied manufacturing methods for preparing amorphous solid dispersions are said to be spray drying and hot melt extrusion. The former process starts from a solution of the drug and a carrier in a common organic solvent or mixture of aqueous and organic solvents. This solution is atomized using a nozzle and the solvent is subsequently quickly evaporated (order of magnitude is milliseconds). The very fast solvent evaporation contributes to the amorphous state of the solid dispersion.

Dallas B. Warren et al. (*Journal of Drug Targeting*, 2010; 18(10): 704-731) have studied the use of water-soluble cellulose ethers as polymeric precipitation inhibitors, such as carboxymethyl cellulose (CMC), methyl cellulose (MC), hydroxyethyl cellulose (HEC), and hydroxypropylmethyl cellulose (HPMC) to improve the absorption of poorly water-soluble drugs.

S. L. Raghavan et al. (International Journal of Pharmaceutics 212 (2001) 213-221), have studied the influence of HPMC, MC, polyvinyl pyrrolidone (PVP) and polyethylene glycol (PEG400) on the crystallization of hydrocortisone acetate (HA).

International Patent Application WO 01/85135 discloses an itraconazole-containing pharmaceutical composition, obtained by spray-drying a solution in which an itraconazole and a pH-independent water-soluble polymer are dissolved into a solvent. WO 01/85135 teaches that the spraying-drying of itraconazole with the water-soluble polymer improves the solubility of itraconazole into water and its pharmaceutical efficacy. Among other water-soluble polymers WO 01/85135 suggests the use of cellulose derivatives, such as methylcellulose, ethylcellulose, hydroxyethyl cellulose, hydroxyethyl methylcellulose, hydroxypropyl methylcellulose, carboxymethyl cellulose, sodium carboxymethyl cellulose, and carboxymethyl ethylcellulose. Methylcellulose, hydroxypropyl methylcellulose, and hydroxypropyl cellulose are said to remarkably increase the water solubility of itraconazole.

International Patent Application WO2008/047201 discloses solid dispersions which comprise a poorly water soluble ionizable drug, a cationic species, and a dispersion polymer, such as hydroxypropyl methylcellulose (HPMC). According to the examples a drug and HPMC (E3 Prem LV; Methocel®, available from The Dow Chemical Company, Midland, Mich.) are mixed with water and methanol to form spray solutions. Solid spray-dried dispersions of the drug in HPMC are produced from this solution. Methocel® E3 Prem LV hydroxypropyl methylcellulose comprises about 29 weight percent of methoxyl groups and about 10 weight percent of hydroxypropoxyl groups.

Alternatively, solid dispersions are produced by extrusion, typically hot melt extrusion. In the most common setup a powder blend is introduced via a feeder into a heated barrel with rotating screws, where the powder blend is heated and intensely mixed in the softened or partially or completely melted state and moved towards a die that shapes the melt as strands, films, pellets, tablets or capsules. The amount of heat and shear forces applied, as well as the rate of cooling when the extrudate leaves the die contributes to the physical structure of the solid dispersion. An amorphous solid dispersion is produced when the drug is present in a substantially amorphous, non-crystalline state.

European Patent Application EP 0 872 233 discloses a solid dispersion comprising (a) loviride and (b) one or more pharmaceutically acceptable water-soluble polymers. The solid dispersion is produced by melt-extrusion wherein the components (a) and (b) and optional additives are blended, the blend is heated to obtain a homogeneous melt, the obtained melt is forced through one or more nozzles and the melt is cooled until it solidifies. The solid dispersion product is milled or ground into particles. The particles are then formulated into tablets or capsules. Among the large variety of listed water-soluble polymers hydroxypropyl methyl cellulose (HPMC) is said to be preferred, particularly HPMC 2910 which has about 29 weight percent of methoxyl groups and about 10 weight percent of hydroxypropoxyl groups.

Geert Verreck et al., "Characterization of solid dispersions of itraconazole and hydroxypropylmethylcellulose prepared by melt extrusion, part I", *International Journal of Pharmaceutics* 251 (2003), p. 165-174, discloses that a milled melt extrudate formulation of 40 weight percent of itraconazole and 60 weight percent of HPMC is chemically and physically stable for periods in excess of 6 months as indicated by the absence of degradation products or re-crystallization of the drug.

Another HPMC which is commonly used as an excipient for drugs is HPMC 2208 which has about 22 weight percent of methoxyl groups and about 8 weight percent of hydroxypropoxyl groups.

Unfortunately, HPMC 2910, which has been specifically recommended for producing solid dispersions comprising certain drugs by spray-drying or hot melt extrusion as discussed above, and HPMC 2208 are known to have a narrow thermal processing window. The thermal processing window is defined as the temperature region in which the HPMC is in a relaxed state but has not yet begun appreciable thermal decomposition. For HPMC 2910 and HPMC 2208 the temperature at which the HPMC transitions from a rigid to a relaxed state (glass transition temperature $T_g$) is in excess of 150° C., while the decomposition temperature is as low as 200-250° C. Moreover, tests have shown that it is difficult to form solid dispersions without phase separation when the composition comprises certain drugs like griseofulvin in HPMC 2910 by spray-drying.

Accordingly, it is an object of the present invention to find new solid dispersions comprising an active ingredient in a hydroxyalkyl methylcellulose. It is a preferred object of the present invention to find a new solid dispersion comprising an active ingredient in a hydroxyalkyl methylcellulose which can be produced by extrusion in a reasonably broad processing window and by spray-drying and which is able to improve the aqueous solubility of an active ingredient to about the same or even to a higher extent than HPMC 2910 or HPMC 2208.

SUMMARY

Surprisingly, it has been found that the water solubility and hence the bioavailability of an active ingredient can be significantly increased by providing a solid dispersion comprising the active ingredient in a highly substituted hydroxyalkyl methylcellulose.

Accordingly, one aspect of the present invention is a solid dispersion comprising at least one active ingredient in at least one hydroxyalkyl methylcellulose having a DS of from 1.0 to 2.7 and an MS of from 0.40 to 1.30, wherein DS is the degree of substitution of methoxyl groups and MS is the molar substitution of hydroxyalkoxyl groups.

Another aspect of the present invention is a process for producing a solid dispersion which comprising the steps of
blending a) at least one hydroxyalkyl methylcellulose having a DS of from 1.0 to 2.7 and an MS of from 0.40 to 1.30, wherein DS is the degree of substitution of methoxyl groups and MS is the molar substitution of hydroxyalkoxyl groups, b) one or more active ingredients and c) one or more optional additives, and
subjecting the blend to extrusion.

Yet another aspect of the present invention is a process for producing a solid dispersion which comprises the steps of
blending a) at least one hydroxyalkyl methylcellulose having a DS of from 1.0 to 2.7 and an MS of from 0.40 to 1.30, wherein DS is the degree of substitution of methoxyl groups and MS is the molar substitution of hydroxyalkoxyl groups, b) one or more active ingredients, c) one or more optional additives, and d) an organic liquid diluent to prepare a liquid composition, and
removing liquid diluent from the liquid composition.

DETAILED DESCRIPTION

The solid dispersion of the present invention comprises a hydroxyalkyl methylcellulose. It has a cellulose backbone having β-1,4 glycosidically bound D-glucopyranose repeating units, designated as anhydroglucose units in the context of this invention, which are represented for unsubstituted cellulose by the formula

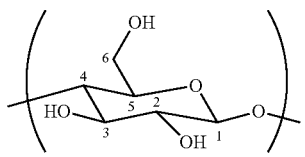

(1)

illustrating the numbering of the carbon atoms in the anhydroglucose units. The numbering of the carbon atoms in the anhydroglucose units is referred to in order to designate the position of substituents covalently bound to the respective carbon atom. At least a part of the hydroxyl groups of the cellulose backbone at the 2-, 3- and 6-positions of the anhydroglucose units are substituted by a combination of methoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the hydroxyalkyl methylcellulose. Preferably a single kind of hydroxyalkoxyl group, more preferably hydroxypropoxyl, is present. Illustrative of the hydroxyalkyl methylcelluloses are hydroxyethyl methylcelluloses, hydroxypropyl methylcelluloses, and hydroxybutyl methylcellulose. Most preferably, the hydroxyalkyl methylcellulose is a hydroxypropyl methylcellulose. The hydroxyl groups of the cellulose backbone at the 2-, 3- and 6-positions of the anhydroglucose units are not substituted by any groups other than methoxyl and hydroxyalkoxyl groups.

The degree of the substitution of hydroxyl groups at the 2-, 3- and 6-positions of the anhydroglucose units by methoxyl groups and hydroxyalkoxyl groups is essential in the present invention.

The average number of methoxyl groups per anhydroglucose unit is designated as the degree of substitution of methoxyl groups, DS. In the definition of DS, the term "hydroxyl groups substituted by methoxyl groups" is to be construed within the present invention to include not only methylated hydroxyl groups directly bound to the carbon atoms of the cellulose backbone, but also methylated hydroxyl groups of hydroxyalkoxyl substituents bound to the cellulose backbone.

The degree of the substitution of hydroxyl groups at the 2-, 3- and 6-positions of the anhydroglucose units by hydroxyalkoxyl groups is expressed by the molar substitution of hydroxyalkoxyl groups, the MS. The MS is the average number of moles of hydroxyalkoxyl groups per anhydroglucose unit in the hydroxyalkyl methylcellulose. It is to be understood that during the hydroxyalkylation reaction the hydroxyl group of a hydroxyalkoxyl group bound to the cellulose backbone can be further etherified by a methylation agent and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone. The term "hydroxyalkoxyl groups" thus has to be interpreted in the context of the MS as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further methylated or not; both methylated and non-methylated hydroxyalkoxyl substituents are included for the determination of MS.

The hydroxyalkyl methylcellulose utilized in the solid dispersion of the present invention has a DS of from 1.0 to 2.7 and an MS of from 0.40 to 1.30. Preferably the hydroxyalkyl methylcellulose has a DS of from 1.0 to 2.3, more preferably from 1.0 to 2.1, most preferably of 1.1 to 2.1 and particularly from 1.6 to 2.1. Preferably the hydroxyalkyl methylcellulose has an MS of from 0.50 to 1.20, more preferably from 0.60 to 1.10. Any preferred range for DS can be combined with any preferred range for MS. Most preferably the hydroxyalkyl methylcellulose has a DS of from 1.6 to 2.1 and an MS of from 0.60 to 1.10. The sum of the DS and MS preferably is at least 1.8, more preferably at least 1.9, most preferable at least 2.5 and preferably up to 3.2, more preferably up to 3.0, most preferably up to 2.9.

The degree of substitution of methoxyl groups (DS) and the molar substitution of hydroxyalkoxyl groups (MS) can be determined by Zeisel cleavage of the hydroxyalkyl methylcellulose with hydrogen iodide and subsequent quantitative gas chromatographic analysis (G. Bartelmus and R. Ketterer, Z. Anal. Chem., 286 (1977) 161-190). When the hydroxyalkyl methylcellulose is hydroxypropyl methylcellulose, the determination of the % methoxyl and % hydroxypropoxyl is carried out according to the United States Pharmacopeia (USP 35, "Hypromellose", pages 3467-3469). The values obtained are % methoxyl and % hydroxypropoxyl. These are subsequently converted into degree of substitution (DS) for methyoxyl substituents and molar substitution (MS) for hydroxypropoxyl substituents. Residual amounts of salt have been taken into account in the conversion.

The hydroxyalkyl methylcellulose utilized in the solid dispersion of the present invention can be in a wide viscosity range. Typically it is in a range from 1.2 to 200,000 mPa·s, measured as a 2 weight-% solution in water at 20° C. according to USP 35, "Hypromellose", pages 3467-3469. It has been found that solid dispersions of the present invention can be prepared by extrusion, typically melt-extrusion, over a wide viscosity range of the hydroxyalkyl methylcellulose. Preferably the viscosity of the hydroxyalkyl methylcellulose utilized in a solid dispersion prepared by extrusion is from 2.4 to 200,000 mPa·s, measured as a 2 weight-% solution in water at 20° C. If the solid dispersion is prepared by spray-drying, the viscosity of the hydroxyalkyl methylcellulose preferably is from 1.2 to 200 mPa·s, more preferably from 1.2 to 100 mPa·s, most preferably from 1.2 to 50 mPa·s, and in particular from 2.4 to 30 mPa·s, measured as a 2 weight-% solution in water at 20° C. Hydroxyalkyl methylcelluloses of such viscosity can be obtained by subjecting a hydroxyalkyl methylcellulose of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982.

The hydroxyalkyl methylcelluloses utilized in the present invention and their use as thickening agents for organic liquids are described in U.S. Pat. No. 4,614,545, but their utility for preparing solid dispersions comprising an active ingredient has been unknown before the present invention. The solid dispersion of the present invention can comprise one or more of the above-described hydroxyalkyl methylcelluloses.

Furthermore, the solid composition of the present invention comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has a minimum aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers.

The hydroxyalkyl methylcelluloses comprised in the solid dispersions of the present invention are able to maintain the concentration of poorly water-soluble active ingredients, such as poorly water-soluble drugs in aqueous solutions at supersaturation levels. A considerably higher concentration of a poorly water-soluble active ingredient in an aqueous solution can be maintained than in the absence of a hydroxyalkyl methylcellulose described above. The degree of supersaturation of a poorly water-soluble active ingredient in an aqueous solution depends on various factors, such as the physical stability and the dissolution rate of a given active ingredient. Dwayne T. Friesen et al. in MOLECULAR PHARMACEUTICS VOL. 5, NO. 6, 1003-1019, 2008 have classified compounds with a structurally diverse range of physicochemical properties on a physical property map Tm/Tg ratio versus log P. The log P value is a standard measure of the lipophilicity of a compound. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as C log P, A log P, and M log P. The Log P may also be estimated using fragmentation methods, such as Crippen's fragmentation method (27 J. Chem. lnf. Comput. Sci. 2 1 (1987)); Viswanadhan's fragmentation method (29 J. Chem. lnf. Comput. Sci. 163 (1989)); or Broto's fragmentation method (19 Eur. J. Med. Chem.-Chim Theor. 7 1 (1984)).

$$\log P_{oct/wat} = \log\left(\frac{[\text{solute}]_{octanol}}{[\text{solute}]_{water}^{un-ionized}}\right)$$

Compounds with high log P values are very hydrophobic and tend to have extremely low water solubilities (often less than 1 μg/mL when their melting points are above about 100° C.) and low propensities for wetting when placed into water.

Tm is the melting temperature and Tg is the glass transition temperature of the compound at atmospheric pressure. Dwayne T. Friesen et al. have divided the compounds into four groups based on their position on this physical property map Tm/Tg ratio versus log P (FIG. 14 on page 1018 in MOLECULAR PHARMACEUTICS VOL. 5, NO. 6, 2008). The first group, Group 1, consists of compounds with relatively low Tm/Tg ratios (<1.25 K/K) and low to moderate log P values (less than about 6); Compounds in Group 2 have somewhat higher Tm/Tg ratios (1.25-1.4) and low to moderate log P values (less than about 6). Compounds in Group 3 have even higher Tm/Tg values (greater than 1.4) and low to moderate log P values (less than about 6). Finally, Group 4 compounds have high log P values (at least about 6).

A preferred aspect of the present invention is a solid dispersion which comprises at least one hydroxyalkyl methylcellulose as described above and additionally at least one active ingredient that has a Tm/Tg ratio of more than 1.0 up to 1.8, preferably more than 1.1 up to 1.6, more preferably from 1.15 up to 1.5, most preferably from 1.25 to 1.40, wherein the melting temperature Tm and the glass transition temperature Tg each are in Kelvin. The active ingredient preferably has a log P of more than 1 up to 11, preferably from 1.5 to 8, most preferably from 2 to 6.

The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

According to one aspect of the invention, the solid dispersion of the present invention is prepared by i) blending a) at least one hydroxyalkyl methylcellulose defined above, b) one or more active ingredients and c) one or more optional additives, and ii) subjecting the blend to extrusion. An extruded solid dispersion is a preferred embodiment of the invention. The term "extrusion" as used herein includes processes known as injection molding, melt casting and compression molding. Techniques for extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The above-mentioned components a), b) and optionally c) are preferably mixed in the form of particles, more preferably in powdered form. The components a), b) and optionally c) may be pre-mixed before feeding the blend into a device utilized for extrusion, preferably melt-extrusion. Useful devices for extrusion, specifically useful extruders, are known in the art. Alternatively, the components a), b) and optionally c) may be fed separately into the extruder and blended in the device before or during a heating step. Preferably components a), b) and optionally c) are pre-blended in an extruder feeder and fed from there into the extruder. The composition or the component(s) that has or have been fed into an extruder are passed through a heated area of the extruder at a temperature which will melt or soften the composition or at least one or more components thereof to form a blend throughout which the active ingredient is dispersed. The blend is subjected to extrusion and caused to exit the extruder. Typical extrusion temperatures are from 50 to 210° C., preferably from 70 to 200° C., more preferably from 90 to 190° C., as determined by the setting for the extruder heating zone(s). An operating temperature range should be selected that will minimize the degradation or decomposition of the active ingredient and other components of the composition during processing. Single or multiple screw extruders, preferably twin screw extruders, can be used in the extrusion process of the present invention. The molten or softened mixture obtained in the extruder is forced through one or more exit openings, such as one or more nozzles or dies. The molten or softened mixture then exits via a die or other such element having one or a plurality of openings, at which time, the extruded blend (now called the extrudate) begins to harden. Since the extrudate is still in a softened state upon exiting the die, it may be easily shaped, molded, chopped, spheronized into beads, cut into strands, tabletted or otherwise processed to the desired physical form. Additionally, the extrudate can be cooled to hardening and ground to a powdered form.

According to another aspect of the invention the solid dispersion of the present invention is prepared by i) blending a) at least one hydroxyalkyl methylcellulose defined above, b) one or more active ingredients, c) one or more optional additives, and d) an organic liquid diluent to prepare a liquid composition, and ii) removing liquid diluent from the liquid composition.

The liquid composition used for preparing the solid dispersion preferably comprises from 1 to 40 weight percent, more preferably from 2.5 to 30 weight percent, most preferably from 5 to 25 weight percent, and particularly from 7 to 20 percent of at least one hydroxyalkyl methylcellulose as described above, from 40 to 99 weight percent, more preferably from 54.9 to 97.4 weight percent, most preferably from 65 to 94.5 weight percent and particularly from 70 to 92 percent of i) an organic liquid diluent or ii) an organic diluent blended with a minor amount of water, e.g. an amount of water described further above, and from 0 to 40 percent, preferably from 0.1 to 40 percent, most preferably from 0.5 to 25 percent, and particularly from 1 to 15 percent of an active ingredient, based on the total weight of the liquid composition. Optional additives, if any, form the remainder of the liquid composition.

The term "organic liquid diluent" as used herein means an organic solvent or a mixture of two or more organic solvents that is liquid at 25° C. and atmospheric pressure. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The liquid composition of the present invention may additionally comprise water; however, the liquid composition should comprise more than 50, more preferably at least 65, and most preferably at least 75 weight percent of an organic liquid diluent and less than 50, more preferably up to 35, and most preferably up to 25 weight percent of water, based on the total weight of the organic liquid diluent and water. Specific examples of preferred organic liquid diluents, optionally mixed with minor amounts of water are: methanol, tetrahydrofuran, methylene chloride, a blend of 80 to 95 weight percent of methanol and 20 to 5 weight percent of water, a blend of 80 to 95 weight percent of tetrahydrofuran and 20 to 5 weight percent of water, a blend of 55 to 85 weight percent of acetone and 45 to 15 weight percent of water, a blend of 15 to 85 weight percent of acetone and 85 to 15 weight percent of methanol, a blend of 15 to 85 weight percent of methyl ethyl ketone and 85 to 15 weight percent of methanol, a blend of 30 to 50 weight percent of acrylonitrile and 70 to 50 weight percent of a $C_{1-4}$-monoalcohol, such as methanol, ethanol, isopropylalcohol, or n-propanol; a blend of 30 to 50 weight percent of methanol and 70 to 50 weight percent of tetrahydrofuran or ethyl acetate, or a blend of 70 to 90 weight percent of ethanol and 10 to 30 weight percent of tetrahydrofuran or ethyl acetate.

Liquid diluent is removed from the liquid composition to prepare the solid dispersion of the present invention. The liquid diluent is the liquid organic diluent, optionally blended with a minor amount of water as described above; i.e., when the composition comprises water as an optional additive, organic liquid diluent and water are removed from the liquid composition to prepare the solid dispersion of the present invention.

A preferred method of removing the liquid diluent from the liquid composition is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7—page 35, line 25.

Other methods of removing the liquid diluent from the liquid composition are by casting the liquid composition into a film or a capsule or by applying the liquid composition onto a solid carrier that also may comprise an active ingredient. In one aspect the liquid composition is contacted with dipping pins for the manufacture of capsules. In another aspect the liquid composition is used for coating dosage forms, such as tablets, granules, pellets, caplets, lozenges, suppositories, pessaries or implantable dosage forms, to form a composition that is coated with the solid dispersion of the present invention. In such a manner drug layering can be achieved, i.e., the dosage form and the coating may comprise different active ingredients for different end-uses and/or having different release kinetics.

By the above-mentioned methods generally a solid amorphous dispersion can be produced wherein at least the major portion, more preferably at least 70 wt %, most preferably at least 90% of the active ingredient is in amorphous form and dispersed in the hydroxyalkyl methylcellulose. The term "amorphous" as used herein means that the active ingredient does not have a long-range three-dimensional translational order. The solid dispersion of the present invention preferably comprises from 20 to 99.9 percent, more preferably from 30 to 98 percent, and most preferably from 50 to 95 percent of a hydroxyalkyl methylcellulose a) as described above, and preferably from 0.1 to 80 percent, more preferably from 2 to 70 percent, and most preferably from 5 to 50 percent of an active ingredient b), based on the total weight of the hydroxyalkyl methylcellulose a) and the active ingredient b). The combined amount of the hydroxyalkyl methylcellulose a) and the active ingredient b) is preferably at least 70 percent, more preferably at least 80 percent, and most preferably at least 90 percent, based on the total weight of the solid dispersion. The remaining amount, if any, are one or more of the adjuvants c) as described below. The solid dispersion can comprise one or more of the hydroxyalkyl methylcelluloses a), one or more of the active ingredients b), and optionally one or more of the adjuvants c), however their total amount is generally within the above-mentioned ranges.

Once the solid dispersion comprising at least one active ingredient in at least one hydroxyalkyl methylcellulose has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms, such as pellets, granules, pills, tablets, caplets, microparticles, fillings of capsules or injection molded capsules or in the form of a powder, film, paste, cream, suspension or slurry. The amount of the active ingredient in the dosage form is generally is at least 0.1 percent, preferably at least 1 percent, more preferably at least 3 percent, most preferably at least 5 percent and generally up to 70 percent or up to 50 percent or up to 30 percent or up to 25 percent, based on the total weight of the dosage form.

Optional additives are preferably pharmaceutically acceptable. Optional additives that may be comprised in the solid dispersion of the present invention are, for example, coloring agents, pigments, opacifiers, flavor and taste improvers, antioxidants, plasticizers, surfactants, lubricants, anti-tack agents, glidants, fillers, disintegrants, binders, salts, such as sodium chloride; saccharides, such as white sugar and lactose; one or more pharmaceutically acceptable polymers different from hydroxyalkyl methylcellulose having a DS of from 1.0 to 2.7 and an MS of from 0.40 to 1.30, and any combination thereof. Useful amounts and types of one or more optional adjuvants are generally known in the art and depend on the intended end-use of the solid dispersion of the present invention. A large variety of optional adjuvants is disclosed in International Patent Application WO 2005/115330, page 45, line 20—page 46, line 33.

The following examples are for illustrative purposes only and are not intended to limit the scope of the present invention. All percentages are by weight unless otherwise specified.

EXAMPLES

The determination of the % methoxyl and % hydroxypropoxyl in hydroxypropyl methylcellulose (HPMC) was carried out according to the United States Pharmacopeia (USP 35, "Hypromellose", pages 3467-3469). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

The viscosity of the samples was measured as a 2% by weight solution in water at 20° C. according to the United States Pharmacopeia (USP 35, "Hypromellose", pages 3467-3469).

Examples 1 and 2 and Comparative Examples A to C: Impact of HPMCs on the Aqueous Solubility of a Poorly Soluble Drug The ability of the HPMCs of Examples 1 and 2 and of Comparative Examples A to C to maintain drug concentrations in an aqueous solution at supersaturation levels was tested with the poorly water soluble drugs Griseofulvin and Phenytoin.

Griseofulvin has a water solubility of 8.54 mg/l, a log P of 2.2, a Tm of 220° C., a Tg of 85° C., and, accordingly a Tm/Tg=493° K/358° K=1.39. [Feng, Tao et. al.; J. Pharm. Sci.; Vol. 97, No. 8, 2008, pg 3207-3221 and W. Curatolo, Pharmaceutical Research, Vol. 26, No. 6, June 2009, pg 1422]. Griseofulvin belongs to group 2 on the map Tm/Tg ratio versus log P (FIG. 14 on page 1018 in MOLECULAR PHARMACEUTICS VOL. 5, NO. 6).

Phenytoin has a water solubility of 32 mg/l, a log P of 2.47, a Tm of 295° C., a Tg of 71° C. and, accordingly a Tm/Tg=568° K/344° K=1.65 [Friesen et al., MOLECULAR PHARMACEUTICS VOL. 5, NO. 6, 1003-1019 and W.

Curatolo, Pharmaceutical Research, Vol. 26, No. 6, June 2009, pg 1422]. Phenytoin belongs to group 3 on the map Tm/Tg ratio versus log P (FIG. 14 on page 1018 in MOLECULAR PHARMACEUTICS VOL. 5, NO. 6, 2008).

Solutions of a HPMC listed in Table 1 below (950 µl, 3.16 mg/L) in phosphate buffered saline (82 mM sodium chloride, 20 mM sodium phosphate dibasic, 47 mM potassium phosphate monobasic, 0.5 wt % simulated intestinal fluid powder, pH 6.5) at 37° C. were robotically delivered into designated 1 mL vials arranged in an aluminum 96 (8×12) well block heated to 37° C. using a Tecan 150 liquid handler. Organic drug solutions at 37° C. were dispensed onto the phosphate buffered saline aqueous solution comprising an HPMC listed in Table 1 below. The organic drug solution was a) 20 g/L griseofulvin in dimethylformamide, 50 µL, final maximum drug concentration of 1000 mg/L, or b) 20 g/L phenytoin in dimethylformamide, 50 µL, final maximum drug concentration of 1000 mg/L. The robot aspirated and dispensed liquid in a set sequence for each vial for about 30 s to mix. After 180 minutes the vials were centrifuged for 1 min at about 3200×g (g=gravitational force on earth). An aliquot (30 µl) was transferred to methanol (150 µl) in a 96-well plate, sealed, briefly gently agitated to mix, and then the drug concentration was analyzed by HPLC.

In a Control Run the experiment was repeated with a phosphate buffered saline aqueous solution which did not contain any amount of HPMC.

In Table 1 below the concentrations of Griseofulvin and Phenytoin are listed that have not precipitated upon centrifugation after 180 minutes but that remain dissolved in the phosphate buffered saline aqueous solution.

The results in Table 1 below illustrate that the HPMCs comprised in the solid dispersions of the present invention are able to maintain the concentration of poorly water-soluble drugs in an aqueous solution at supersaturation levels. A considerably higher drug concentration in an aqueous solution can be maintained than in the Control Run in the absence of an HPMC.

It has surprisingly been found that for some drugs the above-described highly substituted HPMCs having a DS and MS as described further above even have a higher ability to keep the drug at supersaturation levels in an aqueous solution than comparable HPMCs having a lower substitution, specifically a lower MS. For example the drug Griseofulvin, which has a very low water solubility of 8.54 mg/l and belongs to group 2 on the map Tm/Tg ratio versus log P (FIG. 14 on page 1018 in MOLECULAR PHARMACEUTICS VOL. 5, NO. 6, 2008) has a significantly higher concentration in the presence of the HPMCs of Examples 1 and 2 than in the presence of the HPMCs of Comparative Examples A to C.

TABLE 1

| (Comp.) Example | 1 | 2 | A | B | C | Control |
|---|---|---|---|---|---|---|
| Designation | | | HPMC 2910 | HPMC 2910 | HPMC 2208 | — |
| Viscosity at 20° C. [mPa·s] [1] | 2.66 | 4 | 3.1 | 4.3 | 3.1 | — |
| DS | 1.97 | 1.49 | 1.87 | 1.97 | 1.42 | — |
| MS | 0.84 | 0.86 | 0.25 | 0.27 | 0.22 | — |
| % methoxyl | 25.6 | 19.9 | 28.6 | 29.8 | 22.6 | — |
| % hydroxypropoxyl | 26.5 | 27.6 | 9.2 | 9.8 | 8.5 | — |
| Griseofulvin concentration [mg/L] at 180 min. | 833 | 744 | 468 | 389 | 569 | 177 |
| Phenytoin concentration [mg/L] at 180 min. | 219 | 177 | 269 | 506 | 251 | 71 |

[1] measured as 2.0 weight percent solution in water

Examples 1 and 3 to 5 and Comparative Examples A and C: Extrusion

Extrusion with Griseofulvin

Batch Preparation:

0.65 grams of griseofulvin (having a melting temperature of 220° C.) and 5.85 grams of the HPMCs of Examples 1, 3-5 and of Comparative Example C were accurately weighed and transferred to a small propylene bag. The bag was sealed and the formulation was manually blended for 20 seconds by shaking. The material was then transferred from the bag to a weigh boat for easy transfer into the extruder.

Extruder:

Extrusion was performed on a Haake MiniLab II micro compounder utilizing twin co-rotating conical intermeshing advancing flight screws. The unit employed was driven by a 400 W drive motor, has a maximum screw speed of 360 rpm, and is comprised of a single heating zone with a recirculation chamber. The exit port comprises a 2 mm strand die and produced materials were collected as single strands.

Extrusion Operation:

The unit was first heated to the highest operating temperature and prior to the first run was calibrated per the MiniLab manual for torque and pressure. The motor was started, the screw speed set to 100 RPM, and the system placed in cycle mode. The batch was then added through the feed port via a funnel and manually force fed into the extruder using a wooden dowel. Following feeding the pneumatic ram was placed into position and set in the down position. At this point the recirculation time was started. At the completion of the 5 minute recirculation period, the system was placed in flush mode and the extrudate was collected as a single strand onto a Teflon plate. Upon completion of extrusion the strand was cut from the extruder die and allowed to cool to room temperature on the Teflon plate. Collected strands were then manually cut into small pellets using wire cutters.

The results are listed in Table 2 below. Examples 3-5 illustrate that a solid dispersion of the present invention can be prepared by extrusion and results in an extrudate of high quality. Extrusion can be achieved over a wide viscosity range of the highly substituted hydroxyalkyl methylcellulose having a DS and MS as described further above. In contrast thereto, comparable HPMCs of Comparative Examples A and C having a lower substitution could not be extruded at a satisfactory quality, although their viscosity was only 3 mPa s, measured as a 2% by weight solution in water at 20° C.; it is known that a low polymer viscosity facilitates extrusion. HPMCs which have the same DS and MS as Comparative Examples A and C but have a higher viscosity than Comparative Examples A and C will not lead to a better extrudate quality than Comparative Examples A and C.

TABLE 2

| (Comparative) Example | 1 | 3 | 4 | 5 | A | C |
|---|---|---|---|---|---|---|
| HPMC | | | | | HPMC 2910 | HPMC 2208 |
| Viscosity at 20° C. [mPa · s] [1] | 2.66 | 105 | 3768 | 164000 | 3.1 | 3.1 |
| DS | 1.97 | 2.0 | 2.0 | 1.97 | 1.87 | 1.42 |
| MS | 0.84 | 0.85 | 0.85 | 0.84 | 0.25 | 0.22 |
| Operating Parameters | | | | | | |
| Operating Temperature | 165 | 165° C. | 165° C. | 180° C. | 180 | 180 |
| Screw RPM | 60 | 100 | 100 | 100 | 75 | 75 |
| Recirculation (minutes) | 5 | 5 | 5 | 5 | 5 | 5 |
| Extrudate quality | Liquid | Translucent extrudate with minimal browning | Translucent extrudate with minimal browning | Translucent extrudate with minimal browning | Minimal amount of extrudate, poor extrusion, browning | no extrudate exited the die; all material burnt within extruder barrel |

[1] measured as 2.0 weight percent solution in water

Dissolution:

Formulations were assessed for drug release under non-sink conditions in a Varian VK 7010 dissolution apparatus with a corresponding Cary 50 Bio UV-Visible Fiber Optic Spectrophotometer with detection at 290 nm Prior to testing, 900 mL of pH 5.8 phosphate buffer (prepared by dissolving 343.3 g of $KH_2PO_4$ in 50 L of de-ionized water and adding 7.2 g of NaOH to the solution until a final pH of 5.8 was reached) was added to each dissolution vessel and equilibrated to 37° C. via the dissolution water bath. Samples of about 200 mg, corresponding to 20 mg griseofulvin, of the extrudate pellets were weighed on a laboratory balance. At the start of the test, the paddle speed was set to 50 rpm and the pellet samples were added directly to their respective dissolution vessels (n=6 for each formulation). The amount of griseofulvin dissolved was assessed via the fiber optic probes at predetermined time points over a 24 hour period and plotted as Amount Dissolved vs. Time. All three solid dispersions of Examples 3-5 resulted in sustained release of the griseofulvin over time with the rate being dependent upon the viscosity grade used. All three solid dispersions of Examples 3-5 proved capable of achieving and maintaining supersaturation over a 24 hour period, i.e. maintaining more than 8.54 mg/l dissolved griseofulvin (corresponding to 7.69 mg griseofulvin dissolved within 900 mL of pH 5.8 phosphate buffer in the dissolution vessel), which is the saturation solubility of griseofulvin. The amounts of dissolved griseofulvin (in mg) dissolved within 900 mL of pH 5.8 phosphate buffer vs. time is listed in Table 3 below.

TABLE 3

| | (Comparative) Example | | |
|---|---|---|---|
| | 3 | 4 | 5 |
| HPMC viscosity, 2% aq. sol. at 20° C. [mPa · s] | 105 | 3768 | 164000 |
| mg of griseofulvin dissolved in 900 mL of phosphate buffer | | | |
| after 720 minutes | 15.14 | 13.51 | 5.29 |
| after 1440 minutes | 15.57 | 17.50 | 10.39 |

Extrusion with Gliclizide

Example 5 and Comparative Example C were repeated, except that 0.6 grams of gliclizide and 5.4 grams of the HPMC were accurately weighed and the extrusion parameters were listed as in Table 4 below.

TABLE 4

| | (Comparative) Example | |
|---|---|---|
| | 5 | C |
| HPMC | | HPMC 2208 |
| Viscosity at 20° C. [mPa · s] | 164000 | 3.1 |
| DS | 1.97 | 1.42 |
| MS | 0.84 | 0.22 |
| Operating Parameters | | |
| Operating Temperature | 150° C. | 150° C. |
| Screw RPM | 50 | 50 |
| Recirculation (minutes) | 5 | 5 |
| Extrudate quality | Translucent extrudate with minimal browning | Formulation resulted in torque and pressure limits above the systems operating abilities, did not pass material through the die and resulted in a browned product which was removed from the screws |

Examples 1—2 and Comparative Example A: Spray-Drying

Solution Preparation:

Solutions for spray drying containing 2% dissolved solids were prepared by weighing out 9.8 g of a 90/10 (w/w) tetrahydrofuran/water mixture into a glass vessel with Teflon coated stir bar. To the stirred solvent mixture, griseofulvin was added and stirred until fully dissolved. After fully dissolving the griseofulvin, HPMC was added to the stirred solution. The solution was allowed to stir until the HPMC was dissolved. The solutions prepared are detailed in Table 5.

TABLE 5

| HPMC | HPMC Quantity (mg) | Griseofulvin (mg) | Griseofulvin (% of total solids) |
|---|---|---|---|
| Example 1 | 61.1 | 154.1 | 30.4 |
| Example 2 | 61.2 | 143.4 | 29.9 |
| Comp. Example A | 58.5 | 140.6 | 29.4 |

Spray Drying:

Solutions were spray dried on a Bend miniSD spray drying unit. The unit is outfitted with a two-fluid nozzle spray head and a two inch sample collection disc lined with filter paper and ultra dry nitrogen gas as a carrier. Samples were loaded into a 20 mm diameter syringe placed into the miniSD syringe pump. Solution was pumped into the unit at 0.65 mL/min with nitrogen heated to 76° C. flowing at 13.5 slpm. Upon completion of solution spraying the samples were collected into a glass scintillation vial as fine white powder. The vials were placed in a vacuum oven at room temperature and dried for 24 hours to remove residual solvent.

Differential Scanning Calorimetry:

6-8 mg of spray dried formulation were accurately weighed into an aluminum pan and hermetically sealed. A modulated scanning experiment was conducted by modulating the temperature 1.5° C. every 60 seconds. The temperature was held at 25° C. for 5 minutes before beginning a ramp of 3° C./min to a final temperature of 250° C. Glass transitions were observed by examining the reversing heat flow signal. Formulations prepared from Examples 1 and 2 showed a single glass transition temperature in the range of 70-85° C. indicating formation of a solid dispersion. The formulation prepared from Comparative Example A showed two glass transitions, one at 96° C. and another at 144° C. which corresponded to the glass transition of the pure HPMC. The presence of multiple glass transition temperatures indicates phase separation of the formulation components and failure to form a solid dispersion.

Drug Release Testing by Microcentrifuge Test:

Samples of the spray dried formulations were weighed into 2.0 mL conical microcentrifuge tubes in duplicate. Phosphate buffer solution (82 mM sodium chloride, 20 mM sodium phosphate dibasic, 47 mM potassium phosphate monobasic, 0.5 wt % simulated intestinal fluid powder, pH 6.5) at 37° C. was added in an amount that would produce a final concentration of drug of 1000 mg/L if all material was fully dissolved (e.g., 7.2 mg of spray dried dispersion consisting of 1.8 mg drug and 5.4 mg polymer was diluted with 1.8 mL buffer solution). Samples were vortexed 1 mM and set in an isothermal aluminum sample holder set at 37° C. At each time point, samples were centrifuged 1 mM at >13,000×g, and a 50 μl aliquot was removed and diluted with 250 μl methanol. The samples were again vortexed 30 s and held at 37° C. until the next time point. Drug concentration in each aliquot was determined by reverse phase HPLC with UV absorbance detection and the averages of the duplicate runs were calculated.

TABLE 6

| | (Comparative) Example | | |
|---|---|---|---|
| | 1 | 2 | A |
| Viscosity at 20° C. [mPa · s] | 2.66 | 4 | 3.1 |
| mg of griseofulvin dissolved in 900 mL of phosphate buffer after x minutes | | | |
| 4 | 260.5 | 471.9 | 393.9 |
| 10 | 261.9 | 133.7 | 284.2 |
| 20 | 175.4 | 96.8 | 114.7 |
| 360 | 59.0 | 46.0 | 54.7 |

Example 6 and Comparative Example B

Sample Preparation:

Six grams of Danazol and 14 grams of HPMC of Example 6 or of Comparative Example B were dissolved into 180 g of methylene chloride by stirring with a magnetic stir bar overnight. The resulting solutions were cast onto glass plates using a 50 mil (1.27 mm) draw down bar. The resulting films were allowed to dry at room temperature in a fume hood. Dried films were gently peeled from the glass plate and milled into a powder using an Alpine mill.

Drug Release Testing:

Formulations were assessed for drug release under non-sink conditions in a Distek Bio-Dis dissolution apparatus with a corresponding Agilent UV spectrophotometer with detection at 287 nm. 900 mL of pH 7.2 phosphate buffer was added to each dissolution vessel and equilibrated to 37° C. via the dissolution water bath. Samples of about 100 mg of the powdered formulations, along with a control consisting of 30 mg of danazol as received were added into gelatin capsules. At the start of the test, the paddle stirring speed was set to 50 RPM and the capsules were added directly to their respective dissolution vessels (n=3 for each formulation).

TABLE 7

| | (Comparative) Example | | |
|---|---|---|---|
| | 6 | B | Control |
| Viscosity at 20° C. [mPa · s][1)] | 7.7 | 4.3 | — |
| DS | 2.0 | 1.97 | — |
| MS | 0.8 | 0.27 | — |
| Percentage of total Danazol dissolved after x minutes | | | |
| 720 | 13.2 | 6.2 | 4.8 |
| 1440 | 15.7 | 7.2 | 5.1 |

[1)]measured as 2.0 weight percent aqueous solution

The experiments were repeated with using Griseofulvin instead of Danazol. The samples were prepared as described above. Formulations were assessed for drug release under non-sink conditions in a Distek Bio-Dis dissolution apparatus as described above, except that a corresponding Agilent UV spectrophotometer with detection at 254 nm was used.

TABLE 8

| | (Comparative) Example | | |
|---|---|---|---|
| | 6 | B | Control |
| Viscosity at 20° C. [mPa · s] | 7.7 | 4.3 | — |
| DS | 2.0 | 1.97 | — |
| MS | 0.8 | 0.27 | — |
| Percentage of total Griseofulvin dissolved after x minutes | | | |
| 720 | 22.4 | 17.7 | 12.1 |
| 1440 | 21.9 | 17.3 | 12.2 |

What is claimed is:

1. A solid dispersion comprising at least one active ingredient in at least one hydroxyalkyl methylcellulose having a DS of from 1.4 to 2.7, an MS of from 0.60 to 1.10 and a sum of DS and MS of at least 2.5, wherein DS is the degree of substitution of methoxyl groups and MS is the molar substitution of hydroxyalkoxyl groups, wherein the active ingredient is a drug having a Tm/Tg ratio of more than 1.15 and up to 1.5, wherein Tm is the melting temperature and Tg is the glass transition temperature, each in Kelvin.

2. The solid dispersion of claim 1 wherein said at least one hydroxyalkyl methylcellulose has a sum of DS and MS of from 2.5 to 3.2.

3. The solid dispersion of claim 1 wherein said at least one hydroxyalkyl methylcellulose has a viscosity of 105 to 164,000 mPa·s, measured as a 2.0 weight percent solution in water at 20° C.

4. The solid dispersion of claim 3 wherein said at least one hydroxyalkyl methylcellulose has a DS of from 1.6 to 2.1.

5. The solid dispersion of claim 4 wherein the sum of the DS and MS is from 2.5 to 3.2.

6. The solid dispersion of claim 1 in the form of strands, pellets, granules, pills, tablets, caplets, microparticles, fillings of capsules or injection molded capsules or in the form of a powder, film, paste, cream, suspension or slurry.

7. An extruded solid dispersion of claim 1.

8. A process for producing a solid dispersion comprising the steps of
blending a) at least one hydroxyalkyl methylcellulose having a DS of from 1.4 to 2.7, an MS of from 0.60 to 1.10 and a sum of DS and MS of at least 2.5, wherein DS is the degree of substitution of methoxyl groups and MS is the molar substitution of hydroxyalkoxyl groups, b) one or more active ingredients and c) one or more optional additives, and
subjecting the blend to extrusion at a temperature of from 90 to 190° C., wherein the active ingredient is a drug having a Tm/Tg ratio of more than 1.15 and up to 1.5, wherein Tm is the melting temperature and Tg is the glass transition temperature, each in Kelvin.

9. The process of claim 8 wherein the combined amounts of said at least one hydroxyalkyl methylcellulose a) and said one or more active ingredients b) are at least 70 percent, based on the total weight of the blend.

10. A process for producing a solid dispersion comprising the steps of
blending a) at least one hydroxyalkyl methylcellulose having a DS of from 1.4 to 2.7, an MS of from 0.60 to 1.10 and a sum of DS and MS of at least 2.5, wherein DS is the degree of substitution of methoxyl groups and MS is the molar substitution of hydroxyalkoxyl groups, b) one or more active ingredients, c) one or more optional additives, and d) an organic liquid diluent to prepare a liquid composition, and
removing liquid diluent from the liquid composition, wherein the active ingredient is a drug having a Tm/Tg ratio of more than 1.15 and up to 1.5, wherein Tm is the melting temperature and Tg is the glass transition temperature, each in Kelvin.

11. The process of claim 10 wherein the liquid composition is subjected to spray-drying.

12. The process of claim 10 wherein the composition comprises water as an optional additive and the composition comprises more than 50 weight percent of an organic liquid diluent and less than 50 weight percent of water, based on the total weight of organic liquid diluent and water, and wherein organic liquid diluent and water are removed from the liquid composition.

13. An extruded solid dispersion of claim 4.

14. The process of claim 9 wherein said at least one hydroxyalkyl methylcellulose has a DS of from 1.6 to 2.1.

15. The process of claim 11 wherein said at least one hydroxyalkyl methylcellulose has a DS of from 1.6 to 2.1.

16. The solid dispersion of claim 4 wherein the sum of the DS and MS is from 2.5 to 2.9.

17. The process of claim 14 wherein the sum of the DS and MS is from 2.5 to 2.9.

* * * * *